(12) United States Patent
Akashi et al.

(10) Patent No.: US 8,633,032 B2
(45) Date of Patent: *Jan. 21, 2014

(54) NUCLEIC ACID EXTRACTION KIT, NUCLEIC ACID EXTRACTION METHOD, AND NUCLEIC ACID EXTRACTION APPARATUS

(71) Applicant: Toppan Printing Co., Ltd., Tokyo (JP)

(72) Inventors: Shuichi Akashi, Kisarazu (JP); Ryoichi Asai, Tokyo (JP)

(73) Assignee: Toppan Printing Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/770,459

(22) Filed: Feb. 19, 2013

(65) Prior Publication Data

US 2013/0165643 A1    Jun. 27, 2013

Related U.S. Application Data

(63) Continuation of application No. 13/381,817, filed as application No. PCT/JP2010/058557 on May 20, 2010, now Pat. No. 8,404,489.

(30) Foreign Application Priority Data

Jul. 9, 2009   (JP) ................... 2009-162588
Jul. 9, 2009   (JP) ................... 2009-162589

(51) Int. Cl.
 G01N 33/50   (2006.01)
 G01N 1/18    (2006.01)
 B01L 3/00    (2006.01)
 C12N 15/10   (2006.01)

(52) U.S. Cl.
 USPC ............ 436/94; 436/43; 436/174; 436/175; 436/177; 436/178; 436/180; 422/430; 422/63; 422/509; 422/512; 422/527; 422/534; 422/551; 422/552; 422/554; 422/559; 435/6.1; 435/287.1; 435/287.2; 435/287.3; 435/288.3; 435/288.4; 536/25.41

(58) Field of Classification Search
 USPC ......... 436/43, 54, 63, 94, 174, 175, 177, 178, 436/180; 422/430, 63, 68.1, 500, 501, 509, 422/511, 512, 527, 534, 535, 547, 551, 552, 422/554, 559; 435/6.1, 283.1, 287.1, 287.2, 435/287.3, 288.3, 288.4; 536/25.41
 See application file for complete search history.

(56) References Cited

U.S. PATENT DOCUMENTS 5,645,723 A   7/1997  Fujishiro et al.
6,143,250 A  11/2000  Tajima
(Continued)

FOREIGN PATENT DOCUMENTS

CN    101074440    11/2007
JP    9-47278       2/1997
(Continued)

OTHER PUBLICATIONS

Notice of Reasons for Rejection issued Sep. 20, 2011 in corresponding in corresponding Japanese Patent Application No. 2011-521854 (4 pages) (4 pages English translation).

(Continued)

Primary Examiner — Maureen Wallenhorst
(74) Attorney, Agent, or Firm — Staas & Halsey LLP

(57) ABSTRACT

A nucleic acid extraction kit, which enables the nucleic acid extraction operation to be accomplished safely without causing contamination, and in which the complex preparation of reagents and the disposal treatments that are performed before and after the nucleic acid extraction operation can be performed rapidly and simply, with the extraction performed in an automated manner. The nucleic acid extraction kit includes: a container including reagent wells that each store at least a reagent, a sample well into which a biological sample is introduced, a waste liquid well, and a collection well in which an extracted nucleic acid is collected, and an extraction filter cartridge equipped with an extraction filter for separating and extracting a nucleic acid from the biological sample, wherein the extraction filter cartridge is formed in a manner that enables the extraction filter cartridge to be supported on the waste liquid well and the collection well.

16 Claims, 6 Drawing Sheets

(56) References Cited

U.S. PATENT DOCUMENTS

| | | |
|---|---|---|
| 6,337,053 B1 | 1/2002 | Tajima |
| 6,602,474 B1 | 8/2003 | Tajima |
| 7,326,386 B2 | 2/2008 | Sasaki et al. |
| 7,572,578 B2 | 8/2009 | Mori et al. |
| 7,781,205 B2 | 8/2010 | Inana |
| 8,404,489 B2 * | 3/2013 | Akashi et al. .......... 436/94 |
| 2001/0016178 A1 | 8/2001 | Acosta et al. |
| 2005/0045538 A1 | 3/2005 | Seto et al. |
| 2007/0209995 A1 | 9/2007 | Seto et al. |
| 2008/0014610 A1 | 1/2008 | Kamata et al. |
| 2008/0057572 A1 | 3/2008 | Petersen et al. |
| 2010/0276357 A1 | 11/2010 | Mori |
| 2011/0130560 A1 | 6/2011 | Sadri et al. |

FOREIGN PATENT DOCUMENTS

| | | |
|---|---|---|
| JP | 11-258243 | 9/1999 |
| JP | 2001-149097 | 6/2001 |
| JP | 2002-506384 | 2/2002 |
| JP | 2003-066021 | 3/2003 |
| JP | 2005-10179 | 1/2005 |
| JP | 2005-95113 | 4/2005 |
| JP | 2005-101790 | 4/2005 |
| JP | 3635645 | 4/2005 |
| JP | 2005-118020 | 5/2005 |
| JP | 2006-204228 | 8/2006 |
| JP | 2007-101364 | 4/2007 |
| JP | 2011-521854 | 5/2010 |
| WO | WO 98/53912 | 12/1998 |
| WO | WO 2005/118803 A1 | 12/2005 |
| WO | WO 2006/132074 A1 | 12/2006 |
| WO | WO 2007/099937 A1 | 9/2007 |
| WO | WO 2008/156113 A1 | 12/2008 |

OTHER PUBLICATIONS

International Search Report for PCT/JP2010/058557 mailed Aug. 10, 2010.

Japanese Office Communication mailed Dec. 20, 2011 issued in corresponding Japanese Patent Application No. 2011-521854 (3 pages).

US Office Action issued Jul. 9, 2012 in copending parent U.S. Appl. No. 13/381,817 (15 pages).

Notice of Allowance issued Nov. 20, 2012 in copending parent U.S. Appl. No. 13/381,817 (12 pages).

U.S. Appl. No. 13/381,817, filed Dec. 30, 2011, Shuichi Akashi, et al., Toppan Printing Co., Ltd.

Chinese Office Action mailed Jul. 2, 2013 in corresponding Chinese Patent Application No. 201080030093.2 (14 pages) (3 pages English Translation).

* cited by examiner

NUCLEIC ACID EXTRACTION KIT, NUCLEIC ACID EXTRACTION METHOD, AND NUCLEIC ACID EXTRACTION APPARATUS

CROSS REFERENCE TO RELATED APPLICATIONS

This application is a continuation of U.S. patent application Ser. No. 13/381,817 filed Dec. 30, 2011, now U.S. Pat. No. 8,404,489, issued on Mar. 26, 2013, which claimed the benefit under 35 U.S.C. Section 371, of PCT International Application No. PCT/JP2010/058557, filed May 20, 2010, which claimed priority to Japanese Application Nos. 2009-162588 and 2009-162589, filed July, 2009 in the Japanese Patent Office, the disclosures of which are hereby incorporated by reference.

TECHNICAL FIELD

The present invention relates to technology for conducting pretreatments in a method and apparatus used in genetic analysis for concentrating and purifying a nucleic acid extracted from a biological sample and then performing a genetic analysis treatment. Further, the invention relates to a nucleic acid extraction kit that enables the sample supply source and the disposables generated by sample treatment to be discarded during the pretreatment steps without causing contamination, and also relates to a nucleic acid extraction method that uses this extraction kit.

BACKGROUND ART

In recent years, trials have been conducted of introducing genetic analysis into medical settings and the like. These trials have involved testing and analysis of nucleic acids extracted from biological samples. Biological samples refer to various bodily fluids such as blood, plasma, serum, semen and lymphatic fluid, various tissues such as skin, hair and muscle tissue, and various excreted substances such as feces and urine obtained from a target living organism (or the corpse of a living organism), as well as other samples derived from the above samples. Testing of these biological samples offers the possibility of rapid detection of diseases and their pathogenic risk, as well as early detection of infectious diseases and malignant tumors.

Extraction of a nucleic acid from a biological sample is an important process in the fields of genetic engineering and clinical testing. For example, in those cases where a blood or tissue sample is collected from a human body and subjected to clinical testing, only the nucleic acid must be extracted from the biological sample such as the blood sample and then purified. In order to separate the protein and the nucleic acid from the other components, the biological sample is first subjected to a physical or chemical dissolution treatment, and an extraction operation is then used to separate the protein and fats from the nucleic acid, thereby extricating the nucleic acid. During this operation, the process of separating and purifying the protein and the nucleic acid is prone to sample contamination. Organic solvents are widely used in standard extraction methods, but suffer from a number of problems, including toxicity of the solvent itself, the time and effort associated with treating discards, the time and effort associated with centrifugal separation operations, and the possibility of contamination of the sample or infection from the sample.

The BOOM method is one known method for extracting and collecting a nucleic acid. The BOOM method is a nucleic acid extraction technique that combines a chaotropic agent and a solid-phase silica or the like, and utilizes adsorption of the nucleic acid on the silica surface in the presence of chaotropic ions.

In conventional methods, the disruption and extricating step, and the extraction and separation step are performed separately, and because the nucleic acid separation and extraction cannot be performed as part of the pretreatment, the possibilities of infection from the sample and contamination of the sample always exist between the two steps. Moreover, because these operations require human involvement, they tend to be inefficient and complex, and there is a possibility that operators may become infected with pathogens.

One example of an apparatus that uses a solid-phase extraction filter is the nucleic acid extraction apparatus disclosed in Patent Document 1. In Patent Document 1, an integrated column having a plurality of columns arranged in a two-dimensional manner is used to enable a plurality of samples to be treated simultaneously. A vacuum chamber is formed by installing this integrated column (extraction filter cartridge) in an airtight manner at an upper opening of a vacuum chamber, enabling a solid-phase extraction to be performed using the so-called suction method. In those cases where a nucleic acid is to be extracted, the series of steps of adsorbing the nucleic acid to a carrier, washing the carrier, and then desorbing and collecting the nucleic acid from the carrier must be performed.

Further, a technique for independently attaching containers (wells) containing the various reagents used for extracting the nucleic acid, a collection container and a waste liquid container to an apparatus has also been proposed (see Patent Document 2). The nucleic acid extraction apparatus and cartridge disclosed in Patent Document 2 enable treatment to be performed without complex reagent dispensing operations, simply by adding the sample to the apparatus, and is therefore ideal for treating large amounts of a plurality of samples.

However, with the techniques disclosed in the above Patent Documents, considerable time and effort is required in preparing the extraction filter cartridges, collection tubes and waste liquid tubes and the like, and even installing these items on the apparatus requires a significant amount of time. Moreover, in these apparatus, there is possibility of contamination of the surroundings before and after operation of the apparatus. In other words, in the nucleic acid extraction process, a plurality of items such as the integrated column or the various containers and the like must be installed on the apparatus and then removed following use, and therefore there are significant possibilities of splashing of the waste liquid due to vibrations or the like, or foam formation depending on the nature of the solutions, resulting in contamination of the extracted sample. Furthermore, during the disposal process, there is a danger that overturning or deviation of the waste liquid tube installed in the apparatus may cause contamination.

PRIOR ART DOCUMENTS

Patent Documents

Published Japanese Translation of PCT No. 2002-506384
Japanese Patent (Granted) Publication No. 3,635,645

DISCLOSURE OF INVENTION

Problems to be Solved by the Invention

An object of the present invention is to provide a nucleic acid extraction cartridge, a nucleic acid extraction apparatus and a nucleic acid extraction method for extracting a nucleic acid from a sample, which prevent sample contamination, and enable the complex preparation of reagents and disposal treatments that are performed before and after the nucleic acid extraction operation to be performed rapidly and simply, with the extraction performed in an automated manner.

In the present invention, in light of the object described above, wells for storing the reagents, waste liquids and sample, and a nucleic acid separation filter are combined in a single cartridge. By using this cartridge, prior preparation becomes unnecessary, and a simple and rapid nucleic acid extraction method and a simple and safe disposal treatment can be achieved. Specifically, the aspects of the invention described below are achieved.

A first aspect of the present invention is a nucleic acid extraction kit having a container, which includes a reagent well that stores at least a reagent, a sample well into which a biological sample is introduced, a waste liquid well, and a collection well in which an extracted nucleic acid is collected, and an extraction filter cartridge equipped with an extraction filter for separating and extracting a nucleic acid from the biological sample, wherein the extraction filter cartridge is formed in a manner that enables the extraction filter cartridge to be supported on the waste liquid well and the collection well.

A second aspect of the present invention is the nucleic acid extraction kit according to the first aspect, wherein each of the well-forming surfaces on the container is covered with a protective film.

A third aspect of the present invention is the nucleic acid extraction kit according to the first or second aspect, wherein the container includes a holder for housing the extraction filter cartridge.

A fourth aspect of the present invention is the nucleic acid extraction kit according to the third aspect, wherein a member that absorbs liquid is provided on the holder.

A fifth aspect of the present invention is the nucleic acid extraction kit according to the third or fourth aspect, wherein a protective member that covers each of the well-forming surfaces on the container and the extraction filter cartridge is formed with the extraction filter cartridge housed in the holder.

A sixth aspect of the present invention is the nucleic acid extraction kit according to any one of the first through fifth aspects, wherein the waste liquid well is provided with a liquid-absorbent material.

A seventh aspect of the present invention is the nucleic acid extraction kit according to any one of the first through sixth aspects, wherein a wall surface that is higher than the depth to the bottom of each well is provided around the outer periphery of the reagent cartridge, and a mechanism for securing the reagent cartridge to a separate apparatus is provided on the wall surface.

An eighth aspect of the present invention is a nucleic acid extraction method, which is a biological sample pretreatment method that includes a first step of using a reagent to disrupt biological cells and extricating a nucleic acid within a human body fluid and a second step of separating an extricated specific substance from impurities using an extraction filter, and which is a method that employs a container, which includes a reagent well that stores at least a reagent, a waste liquid well and a collection well in which an extracted nucleic acid is collected, and an extraction filter cartridge equipped with an extraction filter for separating and extracting a nucleic acid from a biological sample, wherein the nucleic acid extraction method includes:

a step of eluting a nucleic acid by mixing a biological sample and a reagent, a step of supplying the solution containing the eluted nucleic acid to the extraction filter cartridge which is supported on top of the waste liquid well, a step of retaining the nucleic acid from the solution on the extraction filter cartridge and discarding the solution containing impurities in the waste liquid well, and a step of supporting the extraction filter cartridge on the collection well and collecting the extracted nucleic acid.

A ninth aspect of the present invention is the nucleic acid extraction method according to the eighth aspect, wherein each of the well-forming surfaces on the container is covered with a protective film, and the protective film is pierced during nucleic acid extraction.

A tenth aspect of the present invention is the nucleic acid extraction method according to the eighth or ninth aspect, including a step of removing a solution adhered to the outer surface of the extraction filter cartridge 12.

An eleventh aspect of the present invention is the nucleic acid extraction method according to the tenth aspect, wherein a holder in which the extraction filter cartridge can be installed, and a member that absorbs liquid and is disposed on the holder, are provided on the container, and the step of removing a solution adhered to the outer surface of the extraction filter cartridge involves installing the extraction filter cartridge in the holder and wiping the solution using the member that absorbs liquid.

A twelfth aspect of the present invention is the nucleic acid extraction method according to any one of the eighth to eleventh aspects, wherein in the step of discarding the solution containing impurities in the waste liquid well, pressure is applied using compressed air to discard a portion of the solution and retain a portion of the solution.

A thirteenth aspect of the present invention is a nucleic acid extraction apparatus, having a reagent well that stores at least a reagent, a sample well into which a biological sample is introduced, a waste liquid well, a collection well in which an extracted nucleic acid is collected, and a cartridge that can be supported on the waste liquid well and the collection well and is equipped with an extraction filter for separating and extracting a nucleic acid from the biological sample, and also containing an extraction filter pressurization device for causing a liquid to flow through the extraction filter, a device for moving the cartridge, and a dispensing device for moving liquid reagents and samples.

A fourteenth aspect of the present invention is the nucleic acid extraction apparatus according to the thirteenth aspect, wherein the reagent well, the sample well, the waste liquid well and the collection well are formed within a single container, and the container is installed on a detachable fixed base.

A fifteenth aspect of the present invention is the nucleic acid extraction apparatus according to the thirteenth or fourteenth aspect, wherein the extraction filter pressurization device uses a compressed air supply mechanism to supply compressed air from above the cartridge, thereby causing a liquid to flow through the extraction filter.

A sixteenth aspect of the present invention is the nucleic acid extraction apparatus according to the fifteenth aspect, wherein the compressed air supply mechanism is equipped with an electronic control regulator that enables arbitrary setting of the compressed air applied pressure.

A seventeenth aspect of the present invention is the nucleic acid extraction apparatus according to any one of the thirteenth to sixteenth aspects, wherein the apparatus is provided with a holder for housing the cartridge.

An eighteenth aspect of the present invention is the nucleic acid extraction apparatus according to any one of the thirteenth to seventeenth aspects, wherein the dispensing device employs a dispensing pipette composed of a dispensing nozzle equipped with aspiration and discharge mechanisms, and a detachable dispensing pipette tip that is provided at the tip of the dispensing nozzle.

A nineteenth aspect of the present invention is a nucleic acid extraction method that uses the nucleic acid extraction apparatus according to any one of the thirteenth to eighteenth aspects, wherein the nucleic acid extraction method includes a step of eluting the nucleic acid using the dispensing device to add a biological sample that has been introduced into the sample well to a well containing a reagent for eluting the nucleic acid, a step of adding the solution containing the eluted nucleic acid to the cartridge, which has been supported above the waste liquid well using the device for moving the cartridge, using the dispensing device, a step of retaining the nucleic acid from the solution and discarding the solution containing impurities into the waste liquid well using the extraction filter pressurization device, and a step of collecting the extracted nucleic acid from the cartridge, which has been supported above the collection well using the device for moving the cartridge.

A twentieth aspect of the present invention is the nucleic acid extraction method according to the nineteenth aspect, wherein each of the well-forming surfaces is covered with a protective film, and the protective film is pierced during nucleic acid extraction.

A twenty first aspect of the present invention described in claim 7 or 8 is the nucleic acid extraction method according to the nineteenth or twentieth aspect, wherein in the step of discarding the solution containing impurities into the waste liquid well, pressure is applied using compressed air to discard a portion of the solution containing impurities and retain a portion of the solution.

A twenty second aspect of the present invention is the nucleic acid extraction method according to any one of the nineteenth to twenty first aspects, wherein a holder in which the cartridge can be installed, and a member that absorbs liquid and is disposed on the holder, are provided in the nucleic acid extraction apparatus, and a step of removing a solution adhered to the outer surface of the extraction filter cartridge is performed by installing the extraction filter cartridge in the holder and wiping the solution using the member that absorbs liquid.

A twenty third aspect of the present invention is the nucleic acid extraction method according to any one of the nineteenth to twenty second aspects, wherein following the step of collecting the nucleic acid, residual biological sample liquid left in the sample well is aspirated and transported to the waste liquid well.

Effect of the Invention

According to the present invention, by supporting an extraction filter for extracting a nucleic acid directly on a reagent container in such a manner that enables extraction to be performed, and then integrating these components into a single unit, the instruments used in a single nucleic acid extraction operation can be simplified, and the operations requiring human input can be simplified. Moreover, by providing, within the container, a waste liquid well into which reagents can be discarded, reagent preparation and waste liquid treatment following the nucleic acid collection can be simplified in those cases where an automated nucleic acid extractor is used, enabling the nucleic acid extraction to be performed rapidly, simply, and with no contamination.

Moreover, according to the nucleic acid extraction apparatus of the present invention, reagent preparation and waste liquid treatment following the nucleic acid collection can be simplified in those cases where an automated nucleic acid extractor is used, enabling the nucleic acid extraction to be performed rapidly, simply, and with no contamination. More specifically, by installing a cartridge equipped with an extraction filter directly on top of the waste liquid well and collection well, and then performing the separation and extraction operations using these structural elements, contamination caused by solution splashing due to extraction filter pressurization or overturning of the extraction filter members can be eliminated, enabling the extraction operation to be simplified.

BEST MODE FOR CARRYING OUT THE INVENTION

1. Nucleic Acid Extraction Apparatus

Figure 1:
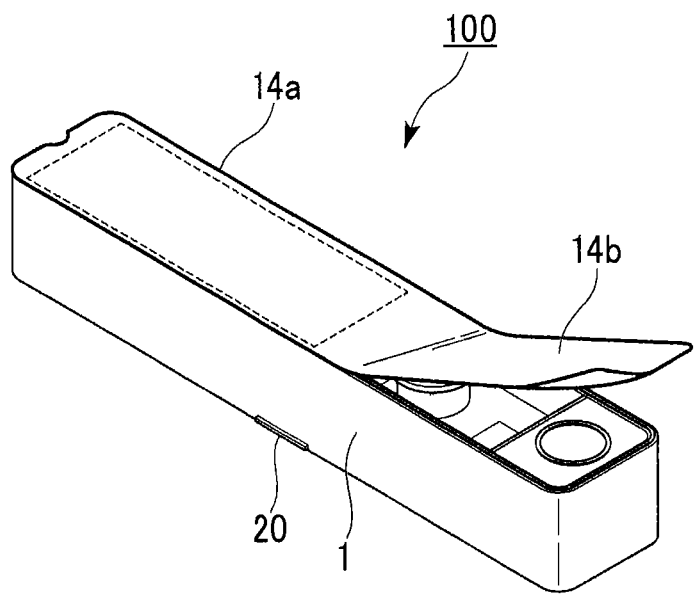
FIG. 1 is a perspective view illustrating the waste liquid side of the main body of a reagent cartridge according to the present invention.
Figure 2:
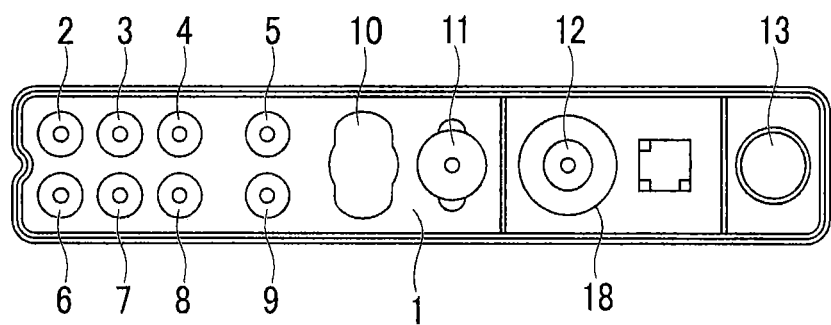
FIG. 2 is a schematic view of the main body of the reagent cartridge illustrated in FIG. 1.

The present invention is described below based on the drawings. FIG. 1 is a perspective view of one embodiment of a reagent cartridge according to the present invention. FIG. 2 is a plan view illustrating each of the well-forming surfaces of the container of the reagent cartridge. As described below, by supplying a biological sample to the sample well of a reagent cartridge 100 and then installing the cartridge in the nucleic acid extraction apparatus, the nucleic acid extraction operation can be performed in an automated manner. A reagent container 1 that constitutes the reagent cartridge of the present invention is composed of a base material that forms the container, in which are formed reagent wells 2 to 8, a waste liquid well 10 in which unnecessary solutions separated during the extraction process are discarded, a collection well 11 for collecting the extracted nucleic acid, and a sample well 13 into which the biological sample is introduced. Each of the reagent wells contains a liquid, such as a solvent for dissolving biological matter such as cell membranes or the like, a diluent for diluting solutions, an eluent for eluting the nucleic acid from the carrier, or a washing liquid for washing away unnecessary solutions, although the solutions contained within the wells are not limited to these types of liquids. Moreover, a nucleic acid extraction kit according to the present invention is also provided with an extraction filter cartridge 12 such as that illustrated in FIG. 3, which is independent from the reagent cartridge main body (the reagent container). The reagent cartridge of the present invention is secured to a nucleic acid extraction apparatus 200 such as that illustrated in FIG. 4, enabling an extraction operation using a dispensing pipette to be performed mechanically.

Each of the structural elements of the apparatus are described below. The apparatus and structural elements of the present invention are not limited to the locations and configurations illustrated in the drawings, and may also be combined with other structural elements, provided the actions and effects of the present invention are not impaired.

<Reagent Cartridge Main Body>

The shape of the reagent container 1 may be any shape that can be secured to the nucleic acid extraction apparatus for subsequent use. Examples of the method used for securing the container include providing lugs 20 on the reagent cartridge which can be hooked onto the apparatus to secure the cartridge, although this is not the only possible method. As illustrated in FIG. 2, the reagent container 1 may be formed as a substantially rectangular shape having a region in which the reagent wells are arrayed, a region in which the waste liquid well is formed, a region in which the collection well is formed, and a region in which the sample well is formed. Further, as illustrated in FIG. 1, a wall surface or footing that is higher than the depth to the bottom of each well is preferably provided around the outer periphery of the reagent container, thus forming a stand-alone structure. By employing such a structure, safety can be improved during operation, for example if the container is left standing temporarily by a user, meaning blood contamination or the like caused by the container overturning can be prevented. Moreover, the mechanism for securing the container to the apparatus, such as the lugs 20 mentioned above, may be provided on the wall surface.

The waste liquid well 10 and the collection well 11 each has a shape that enables the extraction filter cartridge 12 to be supported thereon, and the extraction filter cartridge 12 can be secured to both of these wells in a detachable manner. In the present invention, "a shape that enables the extraction filter cartridge to be supported thereon" means that the reagent container secures the extraction filter cartridge in place, preventing overturning or the like. For example, by matching the external shape of the extraction filter cartridge with the shape of the opening of each well (or a portion of the shape), a shape that enables the extraction filter cartridge to be supported thereon can be achieved.

As described below, during the extraction process, the extraction filter cartridge 12 is moved from the waste liquid well 10 to the collection well 11, and therefore the waste liquid well and the collection well are preferably positioned adjacently. By minimizing the movement distance, contamination of the top of the cartridge can be prevented. Further, the reagent wells are mainly used for performing dispensing operations to the extraction filter cartridge when the cartridge is positioned above the waste liquid well, and therefore the waste liquid well and the region in which the reagent wells are formed are also preferably adjacent. This enables contamination to be prevented and also enables the time of the operations to be shortened.

Further, an extraction filter cartridge holder 18 for housing the extraction filter cartridge 12 is preferably provided in the reagent container 1. Because this enables the reagent cartridge to be installed in the apparatus with the extraction filter cartridge already supported in the holder 18, handling is simplified. Furthermore, as described below, by integrating the extraction filter cartridge 12 with the reagent container 1, both the container and the extraction filter cartridge 12 can be covered with a protective member, thereby preventing incorporation of foreign matter or other contamination.

A member that absorbs liquid may be provided in the bottom of the extraction filter cartridge holder 18. This member is positioned so that when the extraction filter cartridge 12 is positioned in the holder, a portion of the outer surface of the extraction filter cartridge main body 12a, and at least the tip thereof, contacts the member. Immediately following those steps in which there is a possibility of a solution adhering to the outer surface of the extraction filter cartridge, by moving the extraction filter cartridge from the position above the waste liquid well back to the extraction filter cartridge holder, the tip of the extraction filter cartridge makes contact with the member that absorbs liquid, enabling any adhered solution to be absorbed and removed, thereby preventing contamination by the adhered waste liquid. Examples of materials that may be used for the member that absorbs liquid include absorbent materials such as filter paper or sponges.

There are no particular limitations on the material used for forming the reagent container 1 provided it has no effect on the sample and reagents and the like, but using a resin material containing any one of polypropylene, polycarbonate or acrylic enables favorable visible light transmittance to be achieved, thus enabling the state of the various solutions to be confirmed. Examples of the polypropylene include homopolypropylene and random copolymers of polypropylene and polyethylene. Examples of the acrylic include poly (methyl methacrylate), and copolymers of methyl methacrylate with another monomer such as another methacrylate ester, an acrylate ester or styrene. Further, using these resin materials enables better tip heat resistance and strength to be obtained.

In the case of a resin material, examples of methods that may be used for forming the container 1 include various resin molding methods such as injection molding and vacuum molding methods, as well as machine cutting methods.

A member that absorbs waste liquid is preferably installed in the waste liquid well 10. By installing this absorbent member, moisture that exists inside the waste liquid well is absorbed, meaning no contamination occurs if the waste liquid well 10 is overturned, and therefore any potential deleterious effects on humans can be prevented. Further, by using an absorbent material that expands in volume upon moisture absorption to absorb the waste liquid, the absorbent material can expand inside the waste liquid well 10, thereby preventing contamination. Examples of the absorbent member include porous materials typified by sponges, and absorbent polymers typified by sodium polyacrylate. Of these, sponges and the like can be altered in size so that the outer diameter of the sponge in its natural state prior to insertion in the waste liquid well is the same as, or slightly larger than, the internal diameter of the waste liquid well, thereby enabling the sponge to be secured in a predetermined position inside the waste liquid well.

<Extraction Filter Cartridge>

The reagent cartridge 100 of the present invention is provided with the extraction filter cartridge 12, which is equipped with an extraction filter for separating and extracting the nucleic acid from the biological sample. The extraction filter cartridge 12 includes at least an extraction filter 12b secured to the extraction filter cartridge main body 12a.

Figure 3:
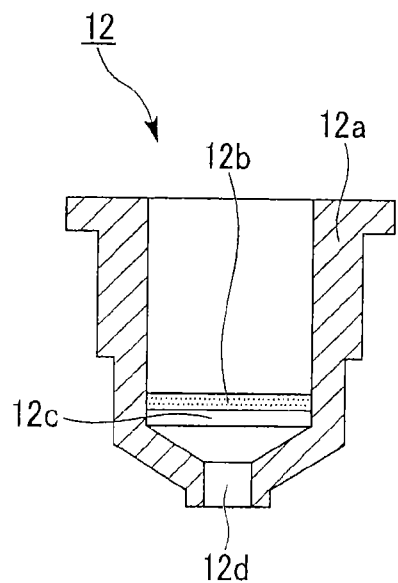
FIG. 3 is a schematic view of an extraction filter cartridge.

One example of the extraction filter cartridge is illustrated in FIG. 3. In the extraction filter cartridge illustrated in FIG. 3, a filter member 12b for adsorbing the nucleic acid is supported in the center of a cylindrical main body 12a that is open at the upper edge, and a filter support 12c is provided directly beneath the filter member 12b to prevent deformation of the filter member 12b. The lower portion of the cylindrical main body 12a located beneath the filter member is formed in a funnel shape, and a nozzle-shaped discharge port 12d that extends for a predetermined length is formed in the center of the lower portion of the main body 12a. The sample solution, washing solution and collection solution described below are dispensed into the upper opening of the extraction filter cartridge, and compressed air is then introduced from the upper opening, thereby forcing each of the solutions through the filter member 12b and the filter support 12c, and then out of the discharge port 12d and into the waste liquid well 10 or collection well 11 described below, where the solution is either discarded or collected.

The filter member 12b of the above-mentioned extraction filter cartridge 12 is formed from a membrane of a porous material that adsorbs the nucleic acid, and is configured so that the nucleic acid is adsorbed and retained during washing with the washing liquid, but is then released as the nucleic acid-adsorbing power of the membrane is weakened during collection using the collection liquid. In the present invention, this porous material includes materials that are combined with fibrous materials such as glass wool. There are no particular limitations on the material of the filter, provided it is capable of adsorbing biological matter in the presence of organic material, although the use of porous materials containing introduced hydroxyl groups as hydrophilic groups is preferable. Silica or other materials having silica combined therewith can be used particularly favorably. The extraction filter cartridge main body 12a can be formed using the same materials and formation methods as the reagent container 1.

The filter support 12c may be laminated beneath and/or above the filter member 12b. The filter member 12b flexes upon pressurization with the pressurization mechanism, resulting in the danger of undesirable partial solution leakage, but by laminating a comparatively rigid filter support 12c, such leakage can be prevented. In terms of the method of preparation, the use of a filter prepared by hardening resin particles by baking is preferable, although the invention is not limited to this particular method, and any filter having pores that enable the material related to the reaction to be retained while the solution passes through the filter can be used. There are no particular limitations on the material for the filter, provided it can be formed in a porous state that enables the solutions to pass through the filter.

<Protective Member>

In order to prevent incorporation of foreign matter or other contamination, a protective member is preferably provided on top of the reagent container 1. In the example of the present invention illustrated in FIG. 1, the open surfaces of the reagent wells 2 to 9 are sealed with a protective film 14a. The protective film 14a covers at least the open surfaces of each of the reagent wells, and a separate film may be provided for each reagent well, a plurality of reagent wells may be covered with a single seal, or the entire region in which the reagent wells are formed may be covered with a single seal.

Moreover, by forming the protective film 14a from a material that has a level of strength that can be pierced by the tip of the dispensing pipette (the dispensing pipette tip) used during the dispensing process, the dispensing pipette can simply be pierced through the protective film 14a from above to extract the reagents from their respective wells during the nucleic acid extraction operation, and therefore there is no need to remove the protective film 14a, and no possibility of reagent contamination.

In order to enable storage of the extraction filter cartridge 12, a second protective member is preferably provided on top of the protective film 14a. In the example of the present invention illustrated in FIG. 1, all of the well-forming surfaces of the reagent container 1, including the sample well 13, the waste liquid well 10, and the extraction filter cartridge holder 18 are covered and sealed with another protective film 14b. Accordingly, introduction of foreign matter into these wells or other contamination can be prevented. By removing the second protective member when the reagent container is installed in the nucleic acid extraction apparatus, operations such as the filling of the sample well 13 with a biological material such as blood can be performed.

By using the above type of structure including a two-stage protective member, protection can be divided between a region that is opened immediately prior to installation within the apparatus, and a region that includes the reagent wells and the like which remains sealed until immediately prior to use. In other words, even after the protective film 14b has been removed, because the protective film 14a still exists on the reagent wells until immediately prior to use, safe storage can be achieved with no risk of contamination.

The protective films 14a and 14b can use any film shape that does not effect the sample or the reagents or the like, and examples include plastic films such as various polypropylenes or polyesters such as polyethylene terephthalate and polynaphthalate, as well as films of metal foil formed from aluminum or the like. The protective film 14a is bonded so as to close the openings of each reagent well, thereby sealing each reagent well. In the case of a plastic film, sealing can be performed by fusing the plastic using heat or a laser. Further, using a material that exhibits transparency for the protective film offers the advantage that, following heat fusion, the sealing properties can be confirmed by visual inspection of the fused surface. The expression that the film "exhibits transparency" means that the film must transmit at least a portion of the visible light spectrum, so that the sealing properties can be confirmed visually. The protective film may have a laminated structure. For example, one side of the film may have an exposed plastic film that acts as the fusion surface, while the other side may be formed from a layer of an inorganic material such as $SiO_2$, thereby improving the sealing properties.

In another embodiment of the protective member, besides the protective film, a portion of the well-forming surfaces of the reagent container 1 including the sample well 13 of the reagent cartridge main body may be provided with a structure that can be opened and closed with a single touch, such as a snap-fit structure. By also employing a similar snap-fit structure on the waste liquid well 10 for when the cartridge is discarded following use, splashing of the sample can be prevented, and the reagent cartridge main body 1 can be disposed of in a safe manner.

<Dispensing Pipette>

In order to prevent contamination, the dispensing pipette used to dispense the reagents is preferably discarded, together with the reagent container 1, following a single extraction of nucleic acid. Accordingly, in the nucleic acid extraction apparatus of the present invention illustrated in FIG. 4, by providing a dispensing nozzle 16 equipped with liquid aspiration and discharge mechanisms separately from a dispensing pipette tip 17 that is detachable from the dispensing nozzle, only the dispensing pipette tip 17 need be discarded.

The dispensing pipette tips are preferably installed in the apparatus in a configuration wherein a plurality of the dispensing pipette tips 17a to 17d which are each used in a single extraction operation of nucleic acid are stored in a dispensing pipette tip rack 21 capable of storing the plurality of dispensing pipette tips. By using this type of structure, when operations have been completed, the dispensing pipette tips can be discarded by simply discarding the entire dispensing pipette tip rack, thereby simplifying the disposal operation.

In the dispensing pipette tip rack 21, a wall surface or footing that is higher than the depth to the bottom of the dispensing pipette tip storage portion is preferably provided around the outer periphery of the dispensing pipette tip rack, thus forming a stand-alone structure. By employing such a structure, safety can be improved during operation, for example if the user leaves the dispensing pipette tip rack standing temporarily, meaning blood contamination or the like caused by the rack overturning can be prevented. Furthermore, a mechanism for securing the dispensing pipette tip rack to the apparatus, such as the lugs described above, may be provided on the wall surface of the stand-alone structure. Moreover, by providing a lid on the dispensing pipette tip storage portion of the dispensing pipette tip rack, contamination by foreign matter prior to use can be prevented, and contamination caused by splashing of solution adhered to the dispensing pipette tips following extraction can also be prevented.

<Nucleic Acid Extraction Apparatus>

Figure 4:
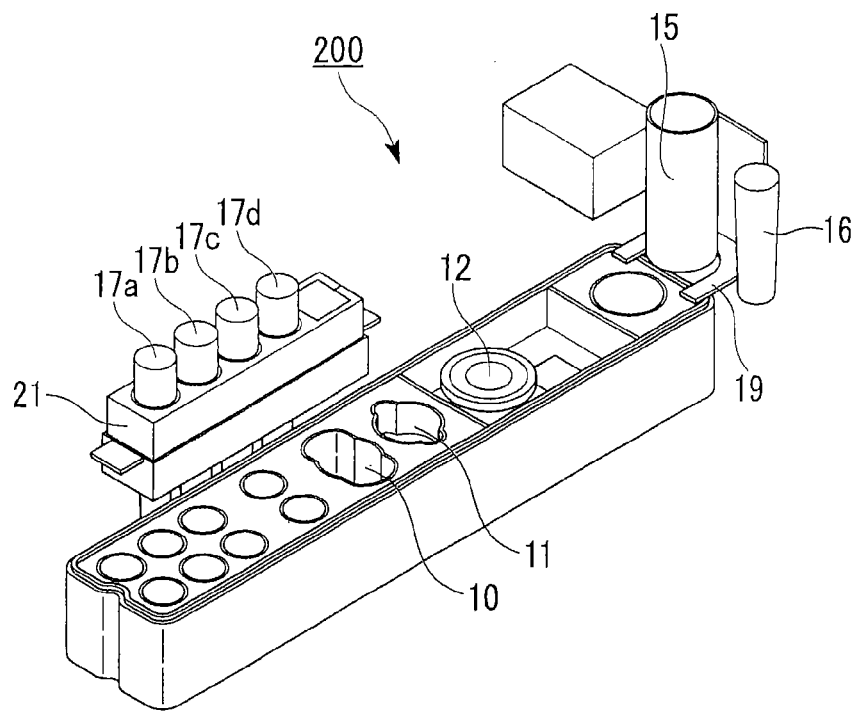
FIG. 4 is a perspective view of a nucleic acid extraction apparatus according to the present invention.

FIG. 4 is a perspective view illustrating the structural elements of a nucleic acid extraction apparatus 200 according to the present invention, which includes the reagent cartridge 100 described above. The nucleic acid extraction apparatus according to the present invention includes at least an extraction filter pressurization device for causing the sample liquid to flow through the extraction filter, a device for moving the extraction filter cartridge, and a dispensing device for moving liquid reagents and samples. The reagent cartridge may be installed on a detachable fixed base prior to use. In the nucleic acid extraction apparatus of the present invention, because the reagent container 1 containing each of the wells, and the extraction filter cartridge 12 can be installed as a single cartridge, the operations following insertion of the cartridge can be automated, enabling the extraction process to be simplified.

However, the apparatus is not limited to the reagent cartridge configuration described above, and in the nucleic acid extraction apparatus of the present invention, by positioning the extraction filter cartridge 12 directly on the waste liquid well 10 and the collection well 11, and performing the separation and extraction operations using each of the structural elements mentioned above, splashing of the solution during pressurization of the extraction filter and contamination caused by overturning of the extraction filter member can be eliminated, and the extraction operation can be simplified. Each of the structural elements is described below in further detail.

The extraction filter pressurization device is a structural element in which, by using a compressed air supply mechanism 15 provided downstream from an air pump and connected to an electronic control regulator to pressurize and then project air or an inert gas such as nitrogen onto the top of the extraction filter cartridge 12, a portion of the solution introduced into the extraction filter cartridge is forced through the extraction filter, thereby achieving separation. By providing the electronic control regulator, the compressed air applied pressure can be set as desired.

The device for moving the extraction filter cartridge is used for moving the extraction filter cartridge 12 from the holder 18 to a position above the waste liquid well 10 or the collection well 11. In the nucleic acid extraction apparatus illustrated in FIG. 4, an extraction filter cartridge support mechanism 19 that is able to support a flange formed on the extraction filter cartridge 12 is provided beneath the compressed air supply mechanism 15, and the pressurization step can be performed by simply using a lift mechanism provided with the movement mechanism to lower the compressed air supply mechanism following completion of the movement.

A dispensing pipette can be used as the dispensing device for dispensing the liquid reagents and samples stored in the various wells. In the nucleic acid extraction apparatus illustrated in FIG. 4, the dispensing device is composed of the dispensing nozzle 16 equipped with liquid aspiration and discharge mechanisms, and the dispensing pipette tip 17, which is the detachable end portion of the dispensing pipette. By providing a plurality of dispensing pipette tips 17a to 17d, the nucleic acid extraction operation can be performed with a single dispensing nozzle, by changing the dispensing pipette tip for each different solution. In this case, a configuration is preferably used in which the dispensing nozzle can be moved to a position above the dispensing pipette tip, and the tip then attached or detached mechanically. The dispensing pipette tips can be stored in a dedicated cartridge, which can be installed on the apparatus either at the same time as, or separately from, the reagent cartridge.

By providing a movement device for the compressed air supply mechanism 15, the extraction filter cartridge support mechanism 19 and the dispensing nozzle 16, the extraction process following installation of the reagent cartridge can be automated. The movement device may use a common movement mechanism, or may be provided with a series of individual movement mechanisms.

Further, the mount (not shown in the drawings) for installing the reagent cartridge 100 on the nucleic acid extraction apparatus may be provided with a heating block. This heating block may be used to heat a portion of the wells of the reagent container 1, thereby accelerating some of the extraction steps.

2. Nucleic Acid Extraction Method

Figure 5:
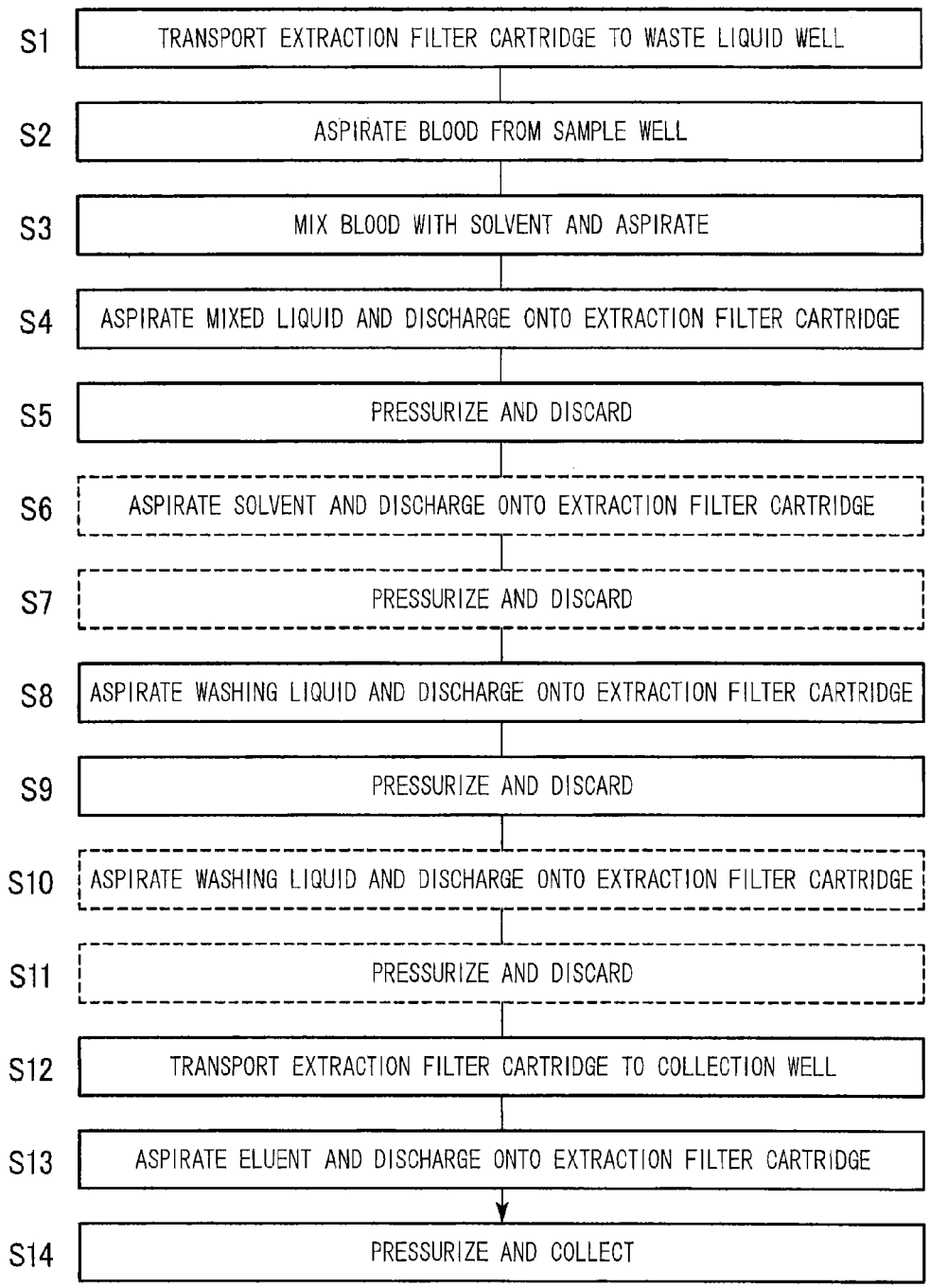
FIG. 5 is a flowchart describing the extraction of a nucleic acid from a sample using the nucleic acid extraction method of the present invention.
Figure 6:
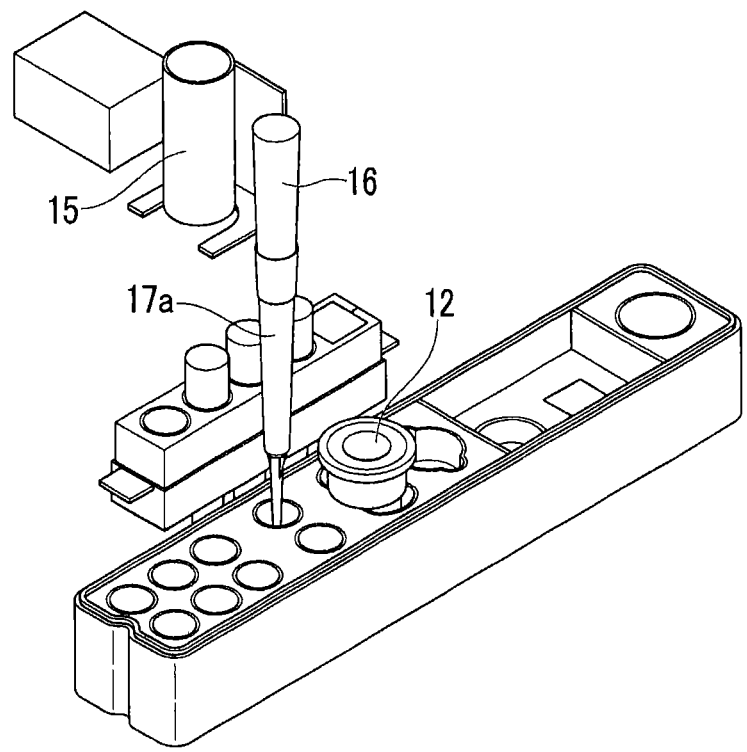
FIG. 6 is a perspective view for describing the nucleic acid extraction method according to the present invention, and illustrates the operation of the apparatus.
Figure 7:
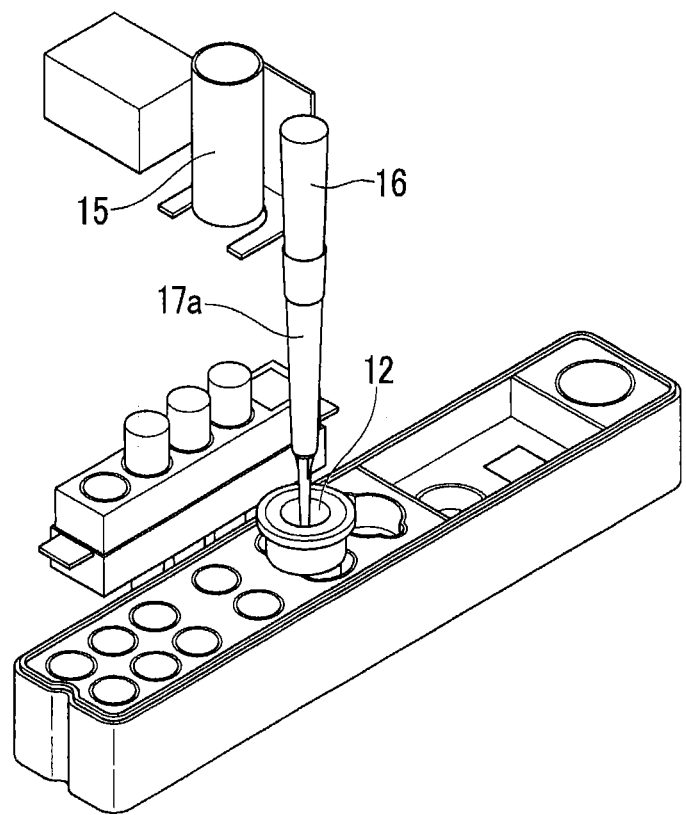
FIG. 7 is a perspective view for describing the nucleic acid extraction method according to the present invention, and illustrates the operation of the apparatus.
Figure 8:
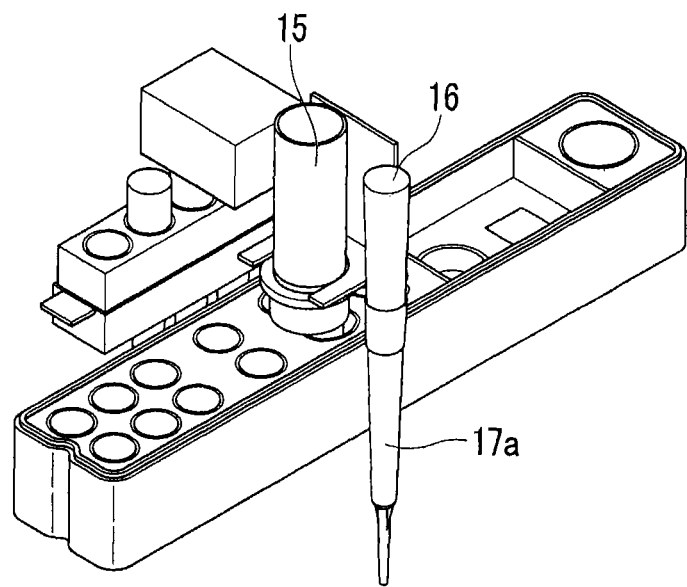
FIG. 8 is a perspective view for describing the nucleic acid extraction method according to the present invention, and illustrates the operation of the apparatus.

A nucleic acid extraction from blood is described below as an example of the nucleic acid extraction method of the present invention, with reference to steps S1 to S14 of the flowchart of FIG. 5, which illustrates the nucleic acid extraction method of the present invention, and the perspective views of FIG. 6 to FIG. 8, which illustrate the operation of the nucleic acid extraction apparatus during the extraction process. Examples of other biological samples besides blood that may be subjected to nucleic acid extraction using the same method include various bodily fluids such as plasma, serum, semen and lymphatic fluid, various tissues such as skin, hair and muscle tissue, and various excreted substances such as feces and urine obtained from a target living organism (or the corpse of a living organism), as well as other samples derived from the above samples. The basic configuration of the nucleic acid extraction method is the same as the widely used BOOM method. The BOOM method is a nucleic acid extraction technique that combines a chaotropic agent with a solid-phase silica or the like, and utilizes the adsorption of the nucleic acid onto the silica surface in the presence of chaotropic ions.

First, the collected blood is injected into the sample well 13 of the reagent cartridge 100, from which the second protective member (the protective film 14b) has been removed. By then installing the reagent cartridge in the nucleic acid extraction apparatus, the operations described below can be controlled electronically and performed in an automated manner. By adopting such a configuration, dispensing operations can be performed using the reagent cartridge main body 1, and the extraction of the biological matter can be automated. In those cases where a dispensing pipette tip cartridge is to be used, this cartridge is also installed on the extraction apparatus.

<Nucleic Acid Extraction Process>

The extraction filter cartridge 12 is moved to a position above the waste liquid well 10 using the device for moving the extraction filter cartridge (S1). The blood added to the sample well 13 is then aspirated using the dispensing pipette (S2). Subsequently, the blood is transported to the solvent within a reagent well and mixed with the solvent to elute the nucleic acid (DNA) from the blood (S3). At this time, by using the tip of the dispensing pipette to pierce the protective film 14a on top of the reagent well before dispensing the blood, the sealing properties of the reagent are maintained until the time of operation, enabling the extraction operation to be performed without any contamination or degradation. The dispensing pipette is used to add the blood to the reagent well 5, which is filled with a chaotropic agent (solvent) that dissolves the biological matter (FIG. 6). The solvent and the blood are mixed thoroughly inside the reagent well by repeatedly discharging and aspirating the mixed liquid using the pipette, thereby dissolving the biological matter.

Next, the dissolved solution is transported to the extraction filter cartridge 12 positioned above the waste liquid well 10 using the dispensing nozzle 16 and the dispensing pipette tip 17, and the solution is then added to the filter member 12b (S4). The nucleic acid eluted from the white blood cells in the blood is adsorbed to the filter member 12b (FIG. 7).

Subsequently, the compressed nozzle 15 is moved above the extraction filter and lowered into place, and compressed air is then used to force the solution containing the non-adsorbed impurities into the waste liquid well as a waste liquid (S5, FIG. 8). At this point, if all of the solution is to be removed from the filter member 12b, then a pressure that is larger than the pressure required to force the solution through the filter must be applied. However, this increased pressure means that there is an extremely high probability of splashing or foaming of the solution, causing contamination of the inside of the apparatus or the operating environment. Accordingly, a lower pressure that does not cause all of the solution to pass through the filter is preferably applied. In other words, in the air pressurization step described above, a portion of the solution containing impurities is retained in the vicinity of the discharge port 12d of the extraction filter cartridge, but by repeating the nucleic acid washing step described below, any residual impurities can be removed. Alternatively, a plurality of elution steps may be provided. In other words, the pipette may be used to aspirate a solvent from another reagent well 4 filled with a chaotropic agent (solvent) and then discharge this solvent onto the extraction filter (S6). Compressed air is then used to force the solution containing the impurities that have not been adsorbed to the filter into the waste liquid well as a waste liquid (S7). By including a plurality of elution steps in this manner, the nucleic acid may be eluted using a pressure that does not result in contamination of the apparatus.

<Nucleic Acid Washing Process>

The washing process for the filter having the adsorbed nucleic acid is performed by aspirating a washing liquid from the reagent well 3 containing the washing liquid using the dispensing device, and then adding the washing liquid to the extraction filter cartridge 12 (S8). Compressed air from the extraction filter pressurization device is then used to force the impurities that have not been adsorbed or bound to the filter into the waste liquid well 10 (S9). The adsorbed nucleic acid is washed repeatedly by repeating this washing process using the washing liquid in the reagent well 7 (S10, S11). In those cases where a plurality of dispensing pipettes (dispensing pipette tips 17) are provided, the pipette tip may be changed each time a different reagent is used during the washing process described above and the collection process described below.

<Collection Process>

The collection well 11 is used for collection of the nucleic acid. First, the extraction filter cartridge 12 is transported by the device for moving the extraction filter cartridge to a position above the collection well 11, in order to enable collection of the nucleic acid in the clean collection well 11 (S12). The eluent in the elution reagent well 9 is then added to the extraction filter cartridge 12 from the dispensing pipette tip 17 of the dispensing device (S13). Then, in a similar manner to that described above, compressed air from the compressed air nozzle 15 is used to collect the nucleic acid eluted from the extraction filter cartridge 12, together with the eluent, in the collection well 11 (S14). The diluent of the regent well 8 may be used to alter the concentration of the collected solution.

Between the nucleic acid extraction process and the collection process, when the extraction filter cartridge is moved from the collection well or the waste liquid well, a step may be provided for removing solution adhered to the outer surface of the extraction filter cartridge 12. By bringing at least a portion of the outer surface of the extraction filter cartridge 12, and particularly the tip of the cartridge in those cases where the cartridge has a funnel-like shape, as the tip is particularly prone to solution adherence, into contact with a member that absorbs liquid, the adhered solution can be removed by wiping. This enables the prevention of contamination caused by adhered waste liquid. As described above, this process can be performed by moving the extraction filter cartridge to the extraction filter cartridge holder 18 which is provided with a member that absorbs liquid, and bringing the extraction filter cartridge into contact with the member that absorbs liquid, thereby absorbing and removing the adhered solution. By employing this type of configuration, a separate mechanism for removing adhered solutions need not be provided, and contamination caused by movement of the extraction filter cartridge can be prevented.

Further, in those cases where excess blood exists in the sample well, a step may be provided for aspirating the excess blood using the pipette, and discarding the blood in the waste liquid well 10. If an absorbent material is provided in the waste liquid well, then no splashing of the liquid occurs, and the reagent container 1 can be discarded without any contamination of the apparatus by the excess blood.

Following completion of this series of automated nucleic acid extraction operations, the nucleic acid may be collected from the collection well 11 using a pipette tip, or may be placed in an automated nucleic acid sequencing apparatus, and transported immediately and automatically to a detection system. By storing the extraction filter cartridge 12 in a predetermined location on the reagent container 1 (either in the holder 18 or above the supporting waste liquid well 10), the entire structure can be discarded safely and simply as medical waste.

As described above, in the present invention, because an integrated nucleic acid extraction cartridge is provided as a nucleic acid extraction kit containing the reagent container 1 and the extraction filter cartridge, once the biological sample has been added to the sample well and the extraction kit has been installed in the nucleic acid extraction apparatus, the nucleic acid extraction operations can be completely automated. Further, because the waste liquid well is formed within the cartridge, no waste liquid is left in the apparatus following the nucleic acid extraction, and treatment of the waste liquid can be simplified. Accordingly, there is no danger of contamination of the apparatus with waste liquid. Furthermore, at least a portion of the wells formed inside the reagent cartridge main body are formed from plastic film, and because the reagents are provided within an integrated cartridge, handling is simple. Moreover, because the cartridge is a single integrated unit, disposal can also be performed safely.

DESCRIPTION OF THE REFERENCE SIGNS

1: Reagent cartridge main body (reagent container)
3: Reagent well (washing liquid)
4: Reagent well (solvent)
5: Reagent well (solvent)
7: Reagent well (washing liquid)
8: Reagent well (diluent)
9: Reagent well (eluent)
10: Waste liquid well
11: Collection well
12: Extraction filter cartridge
12a: Extraction filter cartridge main body
12b: Filter member
12c: Filter support
12d: Discharge port
13: Sample well
14: Protective member
14a: First protective member (protective film)
14b: Second protective member (protective film)
15: Compressed air nozzle
16: Dispensing nozzle
17: Dispensing pipette tip
18: Holder
19: Extraction filter cartridge support mechanism
20: Lug
21: Dispensing pipette tip rack
100: Reagent cartridge
200: Nucleic acid extraction apparatus

The invention claimed is:

1. A nucleic acid extraction kit, having a container comprising
   a reagent well therein that stores at least a reagent,
   a sample well into which a biological sample is introduced,
   a waste liquid well,
   a collection well in which an extracted nucleic acid is collected and an extraction filter cartridge comprising
   an extraction filter for separating and extracting a nucleic acid from the biological sample, wherein
   the extraction filter cartridge is formed in a manner that enables the extraction filter cartridge to be supported on the waste liquid well and the collection well;
   each well-forming surface on the container is covered with a protective film, the protective film formed from a material that can be pierced;
   the container comprises a holder for housing the extraction filter cartridge in the container;
   a filter member is supported in the extraction filter cartridge; and
   a filter support is provided beneath the filter member.

2. The nucleic acid extraction kit according to claim 1, wherein a member that absorbs liquid is provided on the holder.

3. The nucleic acid extraction kit according to claim 1, wherein the waste liquid well comprises a liquid-absorbent material.

4. The nucleic acid extraction kit according to claim 1, wherein a wall surface that is higher than a depth to a bottom of each well is provided around an outer periphery of the container, and the container comprises a mechanism on the wall surface of the container for securing the container to a separate apparatus.

5. A nucleic acid extraction method, which is a biological sample pretreatment method comprising using a reagent to disrupt biological cells and extricating a nucleic acid within a human body fluid, and separating an extricated nucleic acid from impurities using an extraction filter, and which is a method that employs a container comprising:
   a reagent well therein that stores at least a reagent,
   a sample well into which a biological sample is introduced,
   a waste liquid well,
   a collection well in which an extracted nucleic acid is collected, and an extraction filter cartridge comprising
   an extraction filter for separating and extracting a nucleic acid from a biological sample, and
   the nucleic acid extraction method comprises:
   collecting a biological sample from the sample well in the container with a dispensing device,
   eluting a nucleic acid by mixing the biological sample and the reagent,
   adding a solution containing the eluted nucleic acid to the extraction filter cartridge which is supported on top of the waste liquid well,
   retaining the nucleic acid from the solution on the extraction filter cartridge and discarding a solution containing impurities in the waste liquid well, and
   supporting the extraction filter cartridge on the collection well and collecting the extracted nucleic acid into the collection well, wherein
   each well-forming surface on the container is covered with a protective film;
   the protective film is formed from a material that is pierceable during nucleic acid extraction;
   the container comprises a holder for housing the extraction filter cartridge in the container;
   a filter member is supported in the extraction filter cartridge; and
   a filter support is provided beneath the filter member.

6. The nucleic acid extraction method according to claim 5, further comprising removing a solution adhered to an outer surface of the extraction filter cartridge when the extraction filter cartridge is moved from the collection well or the waste liquid well, wherein
   a holder in which the extraction filter cartridge can be installed, and a member that absorbs liquid and is disposed on the holder are provided in the container, and
   the of removing the solution adhered to the outer surface of the extraction filter cartridge comprises installing the extraction filter cartridge in the holder and wiping the solution using the member that absorbs liquid.

7. The nucleic acid extraction method according to claim 5, wherein in the discarding the solution containing impurities in the waste liquid well, applying pressure to the extraction filter using compressed air to discard a portion of the solution into the waste liquid well and retain a portion of the solution on the filter of the extraction filter cartridge.

8. A nucleic acid extraction apparatus, comprising
   a reagent well therein that stores at least a reagent,
   a sample well into which a biological sample is introduced,
   a waste liquid well,
   a collection well in which an extracted nucleic acid is collected, a cartridge that can be supported on the waste liquid well and the collection well and comprises an extraction filter for separating and extracting a nucleic acid from a biological sample, and the nucleic acid extraction apparatus comprising an extraction filter pressurization device for causing a liquid to flow through the extraction filter, a device for moving the cartridge, and a dispensing device for moving liquid reagents and samples, wherein the reagent well, the sample well, the waste liquid well and the collection well are formed within a container, the container is installed on a detachable base;

the at least one reagent in the reagent well is a reagent for eluting nucleic acid;

each well-forming surface on the container is covered with a protective film, the protective film formed from a material that can be pierced;

a filter member is supported in the extraction filter cartridge; and a filter support is provided beneath the filter member.

9. The nucleic acid extraction apparatus according to claim 8, wherein the extraction filter pressurization device uses a compressed air supply mechanism to supply compressed air from above the cartridge, thereby causing a liquid to flow through the extraction filter.

10. The nucleic acid extraction apparatus according to claim 9, wherein the compressed air supply mechanism comprises an electronic control regulator that enables arbitrary setting of the compressed air applied pressure.

11. The nucleic acid extraction apparatus according to claim 8, wherein the apparatus comprises a holder for housing the cartridge in the container.

12. The nucleic acid extraction apparatus according to claim 8, wherein the dispensing device employs a dispensing pipette composed of a dispensing nozzle equipped with aspiration and discharge mechanisms, and a detachable dispensing pipette tip that is provided at the tip of the dispensing nozzle.

13. A nucleic acid extraction method that uses the nucleic acid extraction apparatus according to claim 8, the nucleic acid extraction method comprising:

collecting a biological sample from a sample well in the container with a dispensing device, eluting the nucleic acid by mixing the biological sample and the reagent using the dispensing device to add a biological sample that has been introduced into the sample well to the reagent for eluting the nucleic acid, adding a solution containing the eluted nucleic acid to the cartridge, which has been supported above the waste liquid well using the device for moving the cartridge, using the dispensing device, retaining the nucleic acid from the solution on the extraction filter and discarding a solution comprising impurities into the waste liquid well using the extraction filter pressurization device, and collecting the extracted nucleic acid into the collection well from the cartridge, which has been supported above the collection well using the device for moving the cartridge, wherein each well-forming surface is covered with a protective film;

the protective film is formed from a material that is pierceable during nucleic acid extraction;

a filter member is supported in the extraction filter cartridge; and a filter support is provided beneath the filter member.

14. The nucleic acid extraction method according to claim 13, wherein in the discarding the solution comprising impurities into the waste liquid well, pressure is applied to the extraction filter using compressed air to discard a portion of the solution comprising impurities into the waste liquid well and retain a portion of the solution on the filter of the cartridge.

15. The nucleic acid extraction method according to claim 13, further comprising removing the solution adhered to outer surface of the cartridge when the cartridge is moved from collection well or the waste liquid well, wherein a holder in which the cartridge can be installed, and a member that absorbs liquid and is disposed on the holder, are provided in the container, and the stop of removing the solution adhered to the outer surface of the cartridge comprises installing the cartridge in the holder and wiping the solution using the member that absorbs liquid.

16. The nucleic acid extraction method according to claim 13, wherein following the collecting the extracted nucleic acid aspirating, residual biological sample liquid left in the sample well and transporting to the waste liquid well.

* * * * *

UNITED STATES PATENT AND TRADEMARK OFFICE
CERTIFICATE OF CORRECTION

PATENT NO. : 8,633,032 B2  
APPLICATION NO. : 13/770459  
DATED : January 21, 2014  
INVENTOR(S) : Akashi et al.

Page 1 of 1

It is certified that error appears in the above-identified patent and that said Letters Patent is hereby corrected as shown below:

In the Specification

Column 1, Line 16, delete "July," and insert -- July 9, --, therefor.

In the Claims

Column 16, Line 51, In Claim 6, delete "the of removing" and insert -- the removing --, therefor.
Column 18, Line 36, In Claim 15, after "and the" delete "stop of".

Signed and Sealed this
Twenty-second Day of July, 2014

Michelle K. Lee
*Deputy Director of the United States Patent and Trademark Office*